United States Patent [19]
Law

[11] 4,173,643
[45] Nov. 6, 1979

[54] SYNERGISTIC MICROBIOCIDAL COMPOSITIONS

[75] Inventor: Andrew B. Law, Levittown, Pa.

[73] Assignee: Rohm and Haas Company, Philadelphia, Pa.

[21] Appl. No.: 906,539

[22] Filed: May 17, 1978

Related U.S. Application Data

[63] Continuation-in-part of Ser. No. 426,881, Dec. 20, 1973, abandoned.

[51] Int. Cl.$^2$ .......................... A01N 9/12; A01N 9/20
[52] U.S. Cl. .................................... 424/270; 424/329
[58] Field of Search ............................... 424/329, 270

[56] References Cited

U.S. PATENT DOCUMENTS

| | | | |
|---|---|---|---|
| 2,694,663 | 11/1954 | Stayner | 424/329 |
| 3,523,121 | 8/1970 | Lewis et al. | 260/306.7 |
| 3,544,580 | 12/1970 | Lewis et al. | 260/302 |
| 3,761,488 | 9/1973 | Lewis et al. | 260/302 |

*Primary Examiner*—Leonard Schenkman

[57] ABSTRACT

Combinations of 4-isothiazolin-3-ones with bactericidal quaternary ammonium salts exhibit synergistic bactericidal activity, particularly in the presence of organic matter.

8 Claims, No Drawings

SYNERGISTIC MICROBIOCIDAL COMPOSITIONS

This application is a continuation-in-part application of United States application Ser. No. 426,881 filed Dec. 20, 1973, now abandoned.

This invention relates to synergistic bactericidal compositions which comprise a 4-isothiazolin-3-one, a strong acid salt complex of a 4-isothiazolin-3-one and a bactericidal quaternary ammonium salt.

Quaternary ammonium compounds, especially those having at least one strongly hydrophobic substituent, are widely used as sanitizing and disinfecting agents. However, these compounds are generally greatly inactivated by the presence of organic matter i.e. animal excrement and by common organic additives, thus minimizing their effectiveness in treating soiled surfaces, in imparting residual activity to easily soilable surfaces, and in protecting formulated products from bactericidal attack.

It has now been found that compositions which comprise a 4-isothiazolin-3-one, a strong acid salt of a 4-isothiazolin-3-one, or a metal salt complex of a 4-isothiazolin-3-one in addition to a bactericidal quaternary ammonium salt are resistant to inactivation by organic matter and organic additives and exhibit a synergistic increase in microbicidal activity. Many of these compositions also show unexpected residual activity, even on soiled surfaces. Thus these compounds find their greatest utility as bactericides, sanitizers, germicides and disinfectants in applications wherein organic matter (animal excrement) causes microbicidal inactivation such as in dairies, barns, sties, chicken coops, swimming pools, etc.

A wide variety of 4-isothiazolin-3-ones can be used in the microbicidal compositions of the invention, including (1) 4-isothiazolin-3-ones of the formula

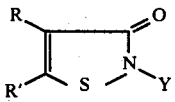 (I)

wherein
Y is a hydrogen atom, an alkyl group, preferably having 1 to 18 carbon atoms, an alkenyl or alkynyl group, preferably having 2 to 18 carbon atoms, and most preferably 2 to 4 carbon atoms, a cycloalkyl group, preferably having 3 to 12 carbon atoms, a single 3 to 8 carbon atom ring, an aralkyl group, preferably having up to 10 carbon atoms, or an aryl group, preferably having up to 10 carbon atoms;
R is a hydrogen atom, a halogen atom, preferably chlorine or bromine, or an alkyl group, preferably having 1 to 4 carbon atoms; and
R' is a hydrogen atom, a halogen atom, preferably chlorine or bromine, or an alkyl group, preferably having 1 to 4 carbon atoms;
(2) salts of 4-isothiazolin-3-ones of Formula I with a strong acid, such as hydrochloric acid, hydrobromic acid, perchloric acid, nitric acid, sulfuric acid, oxalic acid, trichloroacetic acid, p-toluenesulfonic acid, or the like, and (3) metal salt complexes of the formula

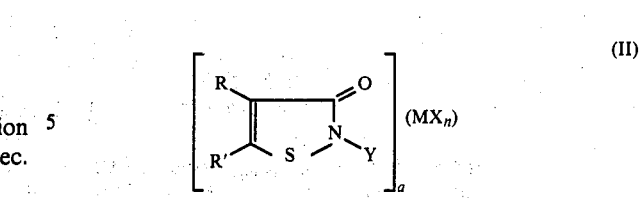 (II)

wherein
Y, R, and R' are as defined above,
M is a cation of a metal, such as barium, cadmium, calcium, chromium, cobalt, copper, iron, lead, lithium, magnesium, manganese, mercury, nickel, sodium, silver, strontium, tin, zinc, or the like;
X is an anion forming a compound with the cation M, wherein the compound has sufficient solubility to form a metal salt complex;
a is the integer 1 or 2; and
n is an integer which, for the anion X, satisfies the valence of the cation M.

As used in the specification and claims, the term alkyl group is intended to include unsubstituted alkyl groups as well as substituted alkyl groups in which one or more of the hydrogen atoms are replaced by a substituent group other than an aryl group. Examples of the substituted alkyl groups which characterize 4-isothiazolin-3-ones and the metal salt complexes of Formulas I and II include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, azacycloalkylalkyl, such as morpholinoalkyl, piperdinoalkyl, and pyrrolidonylalkyl, and the like. The terms alkenyl group and alkynyl group are intended to include unsubstituted alkenyl and alkynyl groups as well as substituted groups such as haloalkenyl, haloalkynyl, and the like.

The term aralkyl group is intended to include unsubstituted aralkyl groups, such as benzyl, phenethyl, methylbenzyl, and the like, such aralkyl groups having one or more of the hydrogen atoms on either the aryl ring of the alkyl chain replaced by another substituent group. Examples of the substituted aralkyl groups which characterizes 3-isothiazolones and the metal salt complexes of Formulas I and II include halogen-, nitro-, ($C_1$–$C_4$)alkyl-, or ($C_1$–$C_4$)alkoxy-substituted aralkyl groups, and the like.

The term aryl group is intended to include unsubstituted aryl groups, such as phenyl, naphthyl, or pyridyl, as well as such aryl groups having one or more of the hydrogen atoms on the aryl ring replaced by another substituent group. Examples of such substituent groups include halogen, cyano, nitro, ($C_1$–$C_4$)alkyl, ($C_1$–$C_4$)alkoxy, ($C_1$–$C_4$)alkylacylamino, ($C_1$–$C_4$)carbalkoxy, sulfamyl, and the like.

Representative Y substituents include hydrogen, methyl, ethyl, propyl, isopropyl, butyl, hexyl, octyl, decyl, pentadecyl, octadecyl, cyclopropyl, cyclohexyl, benzyl, 3,4-dichlorophenyl, 4-methoxybenzyl, 4-chlorobenzyl, phenyl, 3,4-dichlorophenyl, 4-methoxyphenyl, naphthyl, hydroxymethyl, chloromethyl, chloropropyl, diethylaminoethyl, cyanoethyl, carbomethoxyethyl, ethoxyethyl, 2-methoxy-1-bromoethyl, 3,3,5-trimethylcyclohexyl, phenoxyethyl, p-chloroanilino, methyl, phencarbamoxymethyl, hydroxybutyl, allyl, propynyl, vinyl, carboxyethyl, 1-isothiazolinonylethyl, 1,2,2-trichlorovinyl, and the like. Representative R and R' substituents include hydrogen, bromine, chlorine, iodine, methyl, ethyl, propyl, isopropyl, butyl, t-butyl, and the like. The alkyl substituents represented by Y, R, and R' can have either branched- or straight-chain spatial configuration.

Among the anions which X can represent are chloride, bromide, iodide, sulfate, nitrate, nitrite, acetate, chlorate, perchlorate, bisulfate, bicarbonate, oxalate, maleate, p-toluenesulfonate, carbonate, phosphate, and the like. The preferred metals from which M is derived are calcium, copper, magnesium, manganese, nickel, and zinc. Among the metal cations embraced by M are cationic complexes of the metal ions, including complexes with ammonia, simple organic amines, and various heterocyclic organic amines such as pyridines, pyrimidines, and the like.

The preparation and properties of the 4-isothiazolin-3-ones and metal salt complexes of the compositions of the invention are described in United States patent applications Ser. No. 855,046, filed on Sept. 3, 1969, by Sheldon N. Lewis et al., and Ser. No. 142,775, filed on May 12, 1971, by George A. Miller et al., and in U.S. Pat. No. 3,517,022 of George A. Miller et al., granted June 23, 1970, U.S. Pat. No. 3,544,480, of Sheldon N. Lewis et al., granted Dec. 1, 1970, and U.S. Pat. No. 3,761,488, of Sheldon N. Lewis et al., granted Sept. 25, 1973, which are incorporated herein by reference.

In the compositions of the present invention, a particularly useful group of 4-isothiazolin-3-ones are those in which R is a methyl group or a halogen atom, preferably a bromine or chlorine atom. In this group, those compounds in which Y is a substituent having one to eight carbon atoms, and preferably six or seven carbon atoms, such as a hexyl group, a cyclohexyl group, a phenyl group, a halophenyl group, a nitrophenyl group, a benzyl group, or a halobenzyl group, are generally most active, especially in providing good residual activity.

The quaternary ammonium salts which can be used in the microbicidal compositions of the invention are well-known compounds, and include dilower alkyl higher alkyl benzyl ammonium halides, such as dimethyldodecylbenzylammonium chloride, diethyldodecylbenzylammonium chloride, p-diisobutylphenoxyethoxyethyldimethylbenzylammonium chloride, Benzalkon B (dimethyl higher alkyl dichlorobenzyl ammonium chloride), dimethyloctadecyldimethylbenzyl ammonium chloride, and the like, alkyldimethylethylbenzylammonium halides, dilower alkyl dihigher alkyl ammonium halides and trilower alkyl higher alkyl ammonium halides, such as dimethyldidecylammonium chloride, dimethyldidodecylammonium chloride, trimethyltetradecylammonium chloride, methyldiethyldecyloxyethyl ammonium bromide, methyldodecylbenzyltrimethylammonium chloride, methyldodecylxylylenebis(trimethyl)ammonium chloride, and the like, N-trimethyl-N-chloro-N'-benzyl-N'-dodecylglycinamide, N-higher alkyl heterocyclics such as cetylpyridinium chloride, 2-tridecylpyridinium sulfate, 1-hexadecylpyridinium chloride, 2-dodecylisoquinolinium bromide, 2-octyl-1-(2-hydroxyethyl)imidazolinium chloride, 6-dodecyloxybenzylquinolinium chloride, and benzyldecylpiperidinium chloride, and the like. Mixtures of these quaternary ammonium salts can also be used. The preferred quaternary ammonium salts are those having at least one hydrophobic chain of 8 to 18 carbon atoms, most preferably the n-alkyldimethylbenzyl ammonium halides, including mixtures of $C_{12}$-, $C_{14}$- and $C_{16}$-alkyl dimethylbenzyl ammonium halides and substituted-benzyl ammonium halides.

The ratio of 4-isothiazolin-3-one to quaternary ammonium salt in the compositions of the invention and the use levels of the compositions can be varied greatly depending on the degree of total activity desired, the degree of bactericidal contamination to be eradicated, the quantity of organic matter present or to be expected, the nature of the area of surface to be treated, the quaternary ammonium salt and isothiazolin-3-one involved, and related factors. Generally, the weight ratio of 4-isothiazolin-3-one to quaternary ammonium salt will be from about 5:1 to about 1:50, preferably about 1:1 to about 1:15 and most preferably about 1:2 to about 1:7. The upper limits for each of the active components of the microbicidal compositions of the invention are usually related to purely economic considerations. However, when the microbial compositions are to be used as disinfectants rather than as germicides, higher relative levels of the quaternary ammonium salt are generally preferable.

The compositions of the invention can be formulated in any convenient fashion using appropriate solvents such as water, alcohols, glycols, and the like, or mixtures of solvents. For various use applications, it may be advantageous to add suitable surfactants, as well as other conventional additives such as synthetic liquid or solid detergents, stabilizers, anticorrosive agents, extenders and the like. The compositions can be formulated at any desired concentration, the choice of concentration generally being dependent on the particular use conditions which may be anticipated. In general, the compositions will be applied to the locus to be treated at a formulated concentration of about 50 to about 1000 parts per million by weight of quaternary ammonium compound and about ½ to about 200 parts per million by weight of 4-isothiazolin-3-one. However, it should be noted that in some applications, such as for example swimming pools and other aqueous systems, much lower levels, even down to 1 to 2 parts per million, of the quaternary may be used.

The microbicidal compositions of the invention can be used as sanitizers, germicides, and disinfectants in many different applications, on many different surfaces, and in many different environments. These compositions are particularly useful in treating surfaces which have become soiled with organic matter and in providing lasting germicidal protection to environments, such as chicken and turkey coops, barns sties, dairies, and the like, which can become quickly soiled after initial applications of the compositions.

As noted above, the microbicidal compositions of the invention are synergistic—that is, the activity of the compositions is greater than would be expected from the combined individual activity of the 4-isothiazolin-3-one and quaternary ammonium salt. The synergistic activity can be seen in many different ways. For example, in the presence of levels of organic matter which essentially inactivate the quaternary ammonium salt, the combination of quaternary ammonium salt with 4-isothiazolin-3-one possesses greater activity than the 4-isothiazolin-3-one alone. Additionally, the combination of quaternary ammonium salt and 4-isothiazolin-3-one can provide more rapid germicidal action or greater residual activity in the presence of organic matter than either the quaternary or the 4-isothiazolin-3-one alone at the same concentrations.

The following examples will further illustrate the present invention but are not intended to limit it in any way. All temperatures are in degrees Centigrade and percentages and parts are by weight, unless otherwise stated.

EXAMPLE I

To determine the bactericidal effectiveness of the compositions of the invention, the following time-survival test procedure is followed.

At zero time 10 ml. of stock germicide solution (10 times the desired use concentration) are added to 90 ml. of distilled water containing 1 ml. of a 24-hour broth culture of the test organism, plus the desired concentration of sterile, dried, ground, poultry manure. The test container is shaken vigorously to give thorough mixing of the contents.

At each of the selected exposure times, 1 ml. of the medication mixture is removed from the test container and placed in a 9 ml. inactivator blank containing sufficient inactivator to inactivate the highest concentration of each of the germicides under test. In the tests described herein, a mixture of 0.2% lecithin, 1.6% Tween-80, and 0.05% sodium thioglycollate is employed as the inactivating solution.

After thorough mixing, either 1 ml. or serial dilutions of the test solution-inactivating solution mixture are plated with T.G.E. Agar containing additional inactivating mixture.

The above steps are carried out at 25° C. The plates are incubated for 48 hours at 37° C. and then observed for numbers of surviving organisms.

The test organism used are:
(1) *Escherichia coli* (*E. coli* No. 11229). This organism is an indicator of fecal contamination.
(2) *Staphylococus aureus* (*S. aureus* No. 6538).
(3) *Samonella chloreraesuis* (*S. chloreraesuis* No. 10708)
(4) *Enterobactor aerogenes* (*E. aerogenes* No. 15038)

The test germicides used in Examples I to XV are coded as follows:

Q1—n-alkyl($C_{14}$:50%; $C_{12}$:40%; $C_{16}$:10%) dimethylbenzylammonium chloride Q2—a mixture of 50% by weight alkyl ($C_{14}$:60%; $C_{16}$:30%; $C_{12}$:5%; $C_{18}$:5%) dimethylbenzylammonium chloride and 50% alkyl ($C_{12}$:50%; $C_{14}$:30%; $C_{16}$:17%; $C_{18}$:3%) dimethylethylbenzylammonium chloride Q3—a mixture of (n-$C_8$ to n-$C_{18}$) alkyldimethylbenzylammonium chlorides containing not less than 40% by weight n-$C_{12}$ alkyl, not less than 20% n-$C_{14}$ alkyl and not less than 70% by weight total of n-$C_{12}$ and n-$C_{14}$ alkyl. Commercially available under the trademark ROCCAL from Sterling Drug Corporation.

Q4—p-diisobutylphenoxyethoxyethyldimethylbenzylammonium chloride

Q5—a mixture of 80% by weight of methyldodecylbenzyltrimethylammonium chloride and 20% of methyldodecylxylylenebis(trimethyl) ammonium chloride Q6—di-n-alkyl($C_8$—$C_{11}$ n-alkyl, average $C_{10}$) dimethylammonium chloride I1—calcium chloride complex of 5-chloro-methyl 4-isothiazolin-3-one I2—4,5-dichloro-2-cyclohexyl-4-isothiazolin-3-one I3—4-bromo-5-chloro-n-propyl-4-isothiazolin-3-one I4—5-chloro-4-methyl-2-phenyl-4-isothiazolin-3-one I5—4-bromo-5-chloro-2-benzyl-4-isothiazolin-3-one I6—4,5-dichloro-2-n-hexyl-4-isothiazolin-3-one I7—2-n-octyl-4-isothiazolin-3-one I8—5-chloro-2-methyl-4-isothiazolin-3-one I9—2-n-hexyl-4-isothiazolin-3-one I10—5-chloro-4-methyl-2-(3-chlorophenyl)-4-isothiazolin-3-one I11—4,5-dichloro-2-(3,4-dichlorophenyl)-4-isothiazolin-3-one I12—4,5-dichloro-2-(4-chlorophenyl)-4-isothiazolin-3-one I13—4,5-dichloro-2-(2-ethylhexyl)-4-isothiazolin-3-one I14—5-chloro-2-(4-chlorophenyl)-4-methyl-4-isothiazolin-3-one I15—4,5-dichloro-2-n-tetradecyl-4-isothiazolin-3-one I16—4,5-dichloro-2-(3,4-dichlorobenzyl)-4-isothiazolin-3-one I17—4,5-dichloro-2-n-dodecyl-4-isothiazol-3-one I18—4,5-dichloro-2-n-hexadecyl-4-isothiazolin-3-one I19—5-chloro-2-n-tetradecyl-4-isothiazolin-3-one I20—5-chloro-2-n-hexadecyl-4-isothiazolin-3-one I21—4-methyl-2-(4-chlorophenyl)-4-isothiazolin-3-one I22—4-methyl-2-(n-tetradecyl)-4-isothiazolin-3-one I23—4-bromo-2-n-dodecyl-4-isothiazolin-3-one I24—4-bromo-2-(p-chlorobenzyl)-4-isothiazolin-3-one I25—4,5-dibromo-2-n-decyl-4-isothiazolin-3-one I26—4,5-dibromo-2-n-dodecyl-4-isothiazolin-3-one I27—4-bromo-5-chloro-2-(4'-chlorophenyl)-4-isothiazolin-3-one I28—5-chloro-2-t-octyl-4-isothiazolin-3-one I29—4-bromo-5-chloro-2-cyclohexyl-4-isothiazolin-3-one In order to be able to read all the results of each test within a single working day, plates containing less than 100,000 surviving organisms were actually counted whereas plates containing greater than 100,000 surviving organisms were listed as 100,000. Thus, plates listed as 100,000 actually exhibited little control over the test organisms.

TABLE I

| Germicide | Conc. Manure* | Time Survival Test No. of Organisms/ml. of Test Solution After | | | | | |
|---|---|---|---|---|---|---|---|
| | | 5 min. | 10 min. | 30 min. | 24 hrs. | 48 hrs. | 1 wk. |
| Q1 (50 ppm) | none | — | 0 | 0 | 0 | — | — |
| Q1 (50 ppm) | 0.25% | >100,000 | >100,000 | >100,000 | >100,000 | >100,000 | >100,000 |
| Q1 (50 ppm) | 1% | — | >100,000 | >100,000 | >100,000 | — | — |
| Q1 (400ppm) | 1% | — | 182 | 189 | 100,000 | — | — |
| Q1 (50 ppm) + I1(50ppm) | 1% | — | >100,000 | >100,000 | 15,600 | — | — |
| Q1 (100ppm) + I1(50ppm) | 1% | — | >100,000 | >100,000 | 3,640 | — | — |
| Q1 (200ppm) + I1(50ppm) | 1% | — | 43,500 | 20,150 | 0 | — | — |
| Q1 (400ppm) + I1(50ppm) | 1% | — | 403 | 106 | 0 | — | — |
| Q1 (50 ppm) + I2(50ppm) | 1% | — | 12,700 | 314 | 0 | — | — |
| Q1 (100ppm) + I2(50ppm) | 1% | — | 3,510 | 75 | 0 | — | — |
| Q1 (200ppm) + I2(50ppm) | 1% | — | 281 | 0 | 0 | — | — |
| Q1 (400ppm) + I2(50ppm) | 1% | — | 5 | 0 | 0 | — | — |

TABLE I-continued

| Germicide | Conc. Manure* | Time Survival Test No. of Organisms/ml. of Test Solution After | | | | | |
|---|---|---|---|---|---|---|---|
| | | 5 min. | 10 min. | 30 min. | 24 hrs. | 48 hrs. | 1 wk. |
| Q1 (50 ppm) + I2(25ppm) | 0.25% | >100,000 | >100,000 | 2,210 | 0 | 0 | 0 |
| Q1 (50 ppm) + I2(12.5ppm) | 0.25% | >100,000 | >100,000 | 10,000 | 0 | 0 | 0 |
| Q1 (50 ppm) + I2(6.25ppm) | 0.25% | >100,000 | >100,000 | >100,000 | 0 | 0 | 0 |
| Q1 (50ppm) + I2 (3.13ppm) | 0.25% | >100,000 | >100,000 | >100,000 | 0 | 0 | 0 |
| Q1 (50ppm) + I2 (1.5ppm) | 0.25% | >100,000 | >100,000 | >100,000 | 1 | 0 | 0 |
| Q1 (50ppm) + I2 (0.8ppm) | 0.25% | >100,000 | >100,000 | >100,000 | 32 | 0 | 0 |
| Q1 (50ppm) + I2 (0.4ppm) | 0.25% | >100,000 | >100,000 | >100,000 | >100,000 | >100,000 | >100,000 |
| Q1 (50ppm) + I2 (0.2ppm) | 0.25% | >100,000 | >100,000 | >100,000 | >100,000 | >100,000 | >100,000 |
| Q2 (50ppm) | 0.25% | — | 46,800 | 19,500 | >100,000 | — | — |
| Q3 (50ppm) | 0.25% | — | >100,000 | >100,000 | >100,000 | — | — |
| Q4 (50 ppm) | 0.25% | — | >100,000 | >100,000 | >100,000 | — | — |
| Q5 (50 ppm) | 0.25% | — | >100,000 | >100,000 | >100,000 | — | — |
| Q2 (50ppm) + I2 (50ppm) | 0.25% | — | 4,940 | 72 | 0 | — | — |
| Q3 (50 ppm) + I2 (50ppm) | 0.25% | — | 37,700 | 910 | 0 | — | — |
| Q4 (50ppm) + I2 (50ppm) | 0.25% | — | >100,000 | 52,650 | 0 | — | — |
| Q5 (50ppm) + I2 (50ppm) | 0.25% | — | >100,000 | 9,750 | 0 | — | — |

*Sterile dried ground poultry manure
Test Organism = Escherichia coli #11229
No. of Organisms/ml. of Test Solution at Zero Time = Approx. 10,000,000

EXAMPLE II

The following use-dilution test, run at 20° C., is also used to evaluate the bactericidal effectiveness of the compositions of the invention, using test germicides named in Example I.

Five stainless steel rings contaminated in the usual manner with a 48-hour broth culture of *Salmonella chloreraesuis* are dried for one-half hour at 37° C. and then added to five replicate medication tubes containing sterile, dried, ground chicken manure. At zero time, 10 ml. of the test solution is added to the first tube containing the ring and manure, and then to each of the nine remaining tubes, at 30-second intervals.

After one hour exposure to the test solution, the rings are removed at 30-second intervals from five of the ten replicate tubes. As each ring is removed from the test solution, it is placed in another tube containing 10 ml. of sterile inactivator solution (0.2% lecithin, 1.6% Tween-80 and 0.05% sodium thioglycollate).

The inactivator tubes containing the rings are then spun vigorously on a Vortex Mixer to suspend the surviving organisms and 1 ml., 0.1 ml., $10^{-2}$ and $10^{-3}$ dilutions of the resulting suspension are plated with T.G.E. Agar containing inactivator. These plates are also incubated for 48 hours at 37° C.

After all plates have incubated for 48 hours, they are examined to determine the number of colonies present. These figures are then used to calculate the number of surviving organisms per ring.

Table II summarizes typical results of these tests.

TABLE II

| | | Use-Dilution Test | | |
|---|---|---|---|---|
| | Conc. | No. of Organisms Surviving/Ring After | | |
| Germicide (conc-ppm) | Manure* | 1 hr. | 24 hrs. | 48 hrs. |
| Q1 (50ppm) | 0.25% | 8000 | 36000 | 3,800,000 |
| Q1 (50ppm) + I1 (25ppm) | 0.25% | 2580 | — | <10 |
| Q1 (50ppm) + I2 (75ppm) | 0.25% | <10 | <10 | <10 |

*Sterile dried ground poultry manure

EXAMPLE III

The following test procedure is followed to evaluate the residual bactericidal activity of the compositions of the invention, using the germicides identified as above.

A suspension of sterile dried poultry manure in a 24-hour broth culture of *Staphylococcus aureus* or *Enterobactor aerogenes* is applied to the upper surface of a sterile glass microscope slide. The suspension is then dried down on the slide at 37° C. for 1 hour.

Exactly 0.2 ml. of test solution is applied to the contaminated surface of the slide and spread out by means of a wire loop.

The treated slides are placed in a humidity chamber at 25° C. and 87% relative humidity for the desired exposure times. At the end of the indicated exposure times, the slides are placed in sterile petri plates and covered with 20 ml. of inactivator solution (0.1% lecithin, 0.7% Tween-80 and 0.05% sodium thioglycollate). The slides are thoroughly scraped by means of a rubber policeman to remove and suspend surviving organisms. Serial dilutions of the resulting suspensions are then plated with T.G.E. Agar containing additional inactivator. All pates are incubated at 37° C. for 24 or 48 hours.

Following incubation, the Agar plates are observed for numbers of bacterial colonies and these numbers are employed to calculate the number of organisms surviving per slide. The number of organisms surviving per treated slide subtracted from the number of organisms surviving on the control slides (treated with distilled water only) provides the % kill.

Table III summarizes typical results of these tests.

TABLE III

| Bactericidal Activity on Non-Porous Surfaces | | | | |
|---|---|---|---|---|
| | Conc. | Test | No. of Organisms Surviving/Slide After | |
| Germicide | Manure* | Organism | 24 Hours | 48 Hours |
| Q1 (50 ppm) | 0.75% | S. aureus | — | 1,080,000 |
| Q1 (400ppm) | 2.0% | " | 790,000 | — |
| Q1 (50ppm) + I1 (25ppm) | 0.75% | " | — | 6,220 |
| Q1 (400ppm) + I2 (75ppm) | 2.0% | " | <20 | — |
| Q1 (400ppm) | 2.0% | E. aerog. | 175,500,000 | — |
| Q1 (400ppm) + I2 (75ppm) | 2.0% | E. aerog. | <20 | — |

*Sterile dried ground poultry manure

EXAMPLE IV

Following the procedure of Example I, additional 4-isothiazolin-3-ones (I3, I4, I5, I6, I7, I8, I9, and I10)

are evaluated in combination with quaternary (Q1). Table IV summarizes typical results of these tests.

TABLE IV

| | Time Survival Test | | | |
|---|---|---|---|---|
| Germicide (conc-ppm) | Conc. Manure | No. of Organisms Surviving/ ml. of Test Solution After | | |
| | | 10 min. | 30 min. | 24 hr. |
| Q1 (400ppm) | 1% | 500 | 280 | >100,000 |
| Q1 (400ppm) + I3 (50ppm) | 1% | 46 | 0 | 0 |
| Q1 (400ppm) + I4 (50ppm) | 1% | 0 | 0 | 0 |
| Q1 (400ppm) + I5 (50ppm) | 1% | 83 | 0 | 0 |
| Q1 (400ppm) + I6 (50ppm) | 1% | 0 | 0 | 0 |
| Q1 (50ppm) | | >100,000* | >100,000 | >100,000 |
| Q1 (50ppm) + I7 (50ppm) | 0.25% | >100,000* | >100,000 | 2,510 |
| Q1 (50ppm) + I8 (50ppm) | 0.25% | >100,000* | >100,000 | 0 |
| Q1 (50ppm) + I9 (50ppm) | 0.25% | >100,000* | >100,000 | 4 |
| Q1 (50ppm) + I10 (50ppm) | 0.25% | 19,250* | 309 | 0 |

*after 15 minutes
Test Organism = Escherichia coli #11229

The following Examples V through XII utilize the time survival procedure of Example I. These examples further demonstrate the unexpected increased speed-of-kill as well as the prolonged microbicidal activity obtained with combinations of quaternary ammonium salts and 4-isothiazolin-3-ones.

EXAMPLE V

This test demonstrates the initial speed-of-kill and prolonged control obtained for the combination of the quaternary ammonium salt (Q1) and numerous 4-isothiazolin-3-ones, in the presence of sterile dried ground poultry manure. The results of this test are presented in Table V below. These results demonstrate that in the majority of the combinations of quaternary ammonium salts (Q1) with the twenty-three 4-isothiazolin-3-ones that were tested, the combination treatment did possess increased speed-of-kill as compared to the 4-isothiazolin-3-one alone within the time constraints and test conditions of this experiment. The 4-isothiazolin-3-ones I20, I22 and I23 evidently need a longer time interval or lower concentration of poultry manure before reaching their breaking point wherein differences in activity can be seen. An experiment designed to show this is given below in Example XIV. It should be noted that the quaternary amine (Q1) alone gives no control in this test as shown in the results at the bottom of Table V below.

TABLE V

| ISOTHIAZOLONE UNDER TEST | CONC. OF Q1 | CONC. OF ISOTHIAZOLONE | CONC. MANURE* | No. of Organisms Surviving/ ml. of Test Soln. After: | | | |
|---|---|---|---|---|---|---|---|
| | | | | 5 Min. | 10 Min. | 30 Min. | 24 Hrs. |
| I2 | None | 50 ppm | 0.25% | >100,000 | >100,000 | >100,000 | 0 |
| | 50 ppm | 50 ppm | 0.25% | 15,600 | 43 | 1 | 0 |
| I7 | None | 50 ppm | 0.25% | >100,000 | >100,000 | >100,000 | >100,000 |
| | 50 ppm | 50 ppm | 0.25% | >100,000 | >100,000 | >100,000 | 2,510 |
| I8 | None | 50 ppm | 0.25% | >100,000 | >100,000 | >100,000 | 76,050 |
| | 50 ppm | 50 ppm | 0.25% | >100,000 | >100,000 | >100,000 | 0 |
| I9 | None | 50 ppm | 0.25% | >100,000 | >100,000 | >100,000 | >100,000 |
| | 50 ppm | 50 ppm | 0.25% | >100,000 | >100,000 | >100,000 | 4 |
| I11 | None | 50 ppm | 0.25% | >100,000 | >100,000 | 117 | 0 |
| | 50 ppm | 50 ppm | 0.25% | 32,500 | 170 | 0 | 0 |
| I12 | None | 50 ppm | 0.25% | >100,000 | 58,500 | 9,750 | 0 |
| | 50 ppm | 50 ppm | 0.25% | 650 | 0 | 0 | 0 |
| I13 | None | 50 ppm | 0.25% | >100,000 | >100,000 | >100,000 | 0 |
| | 50 ppm | 50 ppm | 0.25% | >100,000 | 52,650 | 184 | 0 |
| I14 | None | 50 ppm | 0.25% | >100,000 | 52,650 | 363 | 0 |
| | 50 ppm | 50 ppm | 0.25% | 199 | 4 | 0 | 0 |
| I15 | None | 50 ppm | 0.25% | >100,000 | >100,000 | >100,000 | >100,000 |
| | 50 ppm | 50 ppm | 0.25% | >100,000 | >100,000 | >100,000 | 10,400 |
| I16 | None | 50 ppm | 0.25% | >100,000 | 58,500 | 32 | 0 |
| | 50 ppm | 50 ppm | 0.25% | 11,050 | 32 | 0 | 0 |
| I 17 | None | 50 ppm | 0.25% | >100,000 | >100,000 | >100,000 | >100,000 |
| | 50 ppm | 50 ppm | 0.25% | >100,000 | >100,000 | >100,000 | 1,500 |
| I 18 | None | 50 ppm | 0.25% | >100,000 | >100,000 | >100,000 | >100,000 |
| | 50 ppm | 50 ppm | 0.25% | >100,000 | >100,000 | 93,600 | 10,400 |
| I 19 | None | 50 ppm | 0.25% | >100,000 | >100,000 | >100,000 | >100,000 |
| | 50 ppm | 50 ppm | 0.25% | >100,000 | >100,000 | >100,000 | 2,570 |
| I 20 | None | 50 ppm | 0.25% | >100,000 | >100,000 | >100,000 | >100,000 |
| | 50 ppm | 50 ppm | 0.25% | >100,000 | >100,000 | >100,000 | >100,000 |
| I 21 | None | 50 ppm | 0.25% | >100,000 | >100,000 | >100,000 | 5 |
| | 50 ppm | 50 ppm | 0.25% | 7,150 | 1,020 | 120 | 0 |
| I 22 | None | 50 ppm | 0.25% | >100,000 | >100,000 | >100,000 | >100,000 |
| | 50 ppm | 50 ppm | 0.25% | >100,000 | >100,000 | >100,000 | >100,000 |
| I 23 | None | 50 ppm | 0.25% | >100,000 | >100,000 | >100,000 | >100,000 |
| | 50 ppm | 50 ppm | 0.25% | >100,000 | >100,000 | >100,000 | |
| I 24 | None | 50 ppm | 0.25% | >100,000 | >100,000 | >100,000 | 1 |
| | 50 ppm | 50 ppm | 0.25% | 6,500 | 313 | 54 | 0 |
| I 25 | None | 50 ppm | 0.25% | >100,000 | >100,000 | >100,000 | >100,000 |
| | 50 ppm | 50 ppm | 0.25% | >100,000 | >100,000 | >100,000 | 64,350 |
| I 26 | None | 50 ppm | 0.25% | >100,000 | >100,000 | >100,000 | >100,000 |

TABLE V-continued

| ISOTHIAZOLONE UNDER TEST | CONC. OF Q1 | CONC. OF ISOTHIAZOLONE | CONC. MANURE* | No. of Organisms Surviving/ml. of Test Soln. After: | | | |
|---|---|---|---|---|---|---|---|
| | | | | 5 Min. | 10 Min. | 30 Min. | 24 Hrs. |
| | 50 ppm | 50 ppm | 0.25% | >100,000 | >100,000 | >100,000 | 2,840 |
| I 27 | None | 50 ppm | 0.25% | >100,000 | >100,000 | >100,000 | 0 |
| | 50 ppm | 50 ppm | 0.25% | >100,000 | 3,900 | 121 | 0 |
| I 28 | None | 50 ppm | 0.25% | >100,000 | >100,000 | >100,000 | >100,000 |
| | 50 ppm | 50 ppm | 0.25% | >100,000 | >100,000 | 16,900 | 1 |
| I 29 | None | 50 ppm | 0.25% | >100,000 | >100,000 | >100,000 | 0 |
| | 50 ppm | 50 ppm | 0.25% | >100,000 | 1,110 | 83 | 0 |
| None | 50 ppm | None | 0.25% | >100,000 | >100,000 | >100,000 | >100,000 |
| None | None | None | 0.25% | >100,000 | >100,000 | >100,000 | >100,000 |

*Sterile dried ground poultry manure
Test Organism - *Escherichia coli*
Average No. of *Escherichia coli* Organisms/ml. of Test Soln. at zero time = 10,000,000

EXAMPLE VI

This test demonstrates that the combination, of quaternary ammonium salt (Q1) and 4-isothiazolin-3-one (I2) in various concentration ratios, gives greater speed-of-kill than the corresponding concentration of 4-isothiazolone (I2) alone or the corresponding quaternary ammonium salt (Q1) alone. The results of this test are given in Table VI below.

TABLE VI

| CONC. OF Q1 | CONC. OF I2 | CONC. MANURE* | No. of Organisms Surviving/ml. of Test Soln. After: | | | |
|---|---|---|---|---|---|---|
| | | | 5 Min. | 10 Min. | 30 Min. | 24 Hrs. |
| 50 ppm | None | 0.25% | >100,000 | >100,000 | >100,000 | >100,000 |
| 50 ppm | 50 ppm | 0.25% | 32,500 | 372 | 23 | 0 |
| 50 ppm | 75 ppm | 0.25% | 2,990 | 133 | 11 | 0 |
| 50 ppm | 100 ppm | 0.25% | 2,660 | 205 | 6 | 0 |
| 50 ppm | 200 ppm | 0.25% | 1,320 | 45 | 2 | 0 |
| None | 50 ppm | 0.25% | >100,000 | >100,000 | >100,000 | 0 |
| None | 75 ppm | 0.25% | >100,000 | >100,000 | >100,000 | 0 |
| None | 100 ppm | 0.25% | >100,000 | >100,000 | >100,000 | 0 |
| None | 200 ppm | 0.25% | >100,000 | >100,000 | 87,750 | 0 |
| None | None | 0.25% | >100,000 | >100,000 | >100,000 | >100,000 |

*Sterile dried ground poultry manure
Test Organism = *E. coli* No. 11229
No. of Organisms/ml. of Test Soln. at zero time = 9,000,000 ing organisms have flourished and multiplied as a result of the nutrients in the poultry manure. Whereas, the combination of (Q1) with (I2) at as low a concentration ratio as 400/1.5 gave complete control for up to 72 hours at concentration levels where the (I2) alone gave no such control. It should be noted that the (I2) alone at 3.13 ppm gave slight control at 24 hours but the organism started to propagate itself within 72 hours of initial treatment.

TABLE VII

| CONC. OF Q1 | CONC. OF I2 | CONC. MANURE* | No. of Organisms Surviving/ml. of Test Solution After: | | | | |
|---|---|---|---|---|---|---|---|
| | | | 5 Min. | 10 Min. | 30 Min. | 24 Hrs. | 72 Hrs. |
| 400 ppm | None | 1.0% | 1,320 | 1,790 | 185 | 14,300 | >100,000 |
| 400 ppm | 3.13 ppm | 1.0% | 2,050 | 1,230 | 286 | 0 | 0 |
| 400 ppm | 1.5 ppm | 1.0% | 2,400 | 930 | 900 | 0 | 0 |
| 400 ppm | 0.8 ppm | 1.0% | 2,770 | 1,180 | 810 | 4 | 3 |
| 400 ppm | 0.4 ppm | 1.0% | 2,440 | 1,310 | 1,120 | 1,820 | 117,000 |
| 400 ppm | 0.2 ppm | 1.0% | 3,130 | 1,540 | 1,300 | 29,250 | >100,000 |
| None | 3.13 ppm | 1.0% | >100,000 | >100,000 | >100,000 | 1,720 | 2,290 |
| None | 1.5 ppm | 1.0% | >100,000 | >100,000 | >100,000 | >100,000 | >100,000 |
| None | 0.8 ppm | 1.0% | >100,000 | >100,000 | >100,000 | >100,000 | >100,000 |
| None | 0.4 ppm | 1.0% | >100,000 | >100,000 | >100,000 | >100,000 | >100,000 |
| None | 0.2 ppm | 1.0% | >100,000 | >100,000 | >100,000 | >100,000 | >100,000 |
| None | None | 1.0% | >100,000 | >100,000 | >100,000 | >100,000 | >100,000 |

*Sterile dried ground poultry manure
Test Organism = *E. coli* No. 11229
No. of Organisms/ml. of Test Solution at zero time = 11,050,000

EXAMPLE VII

This test is analogous to Example VI above except for the fact that a much higher concentration of quaternary ammonium salt (Q1) and poultry manure were used in combination with a much lower concentration of 4-isothiazolin-3-one. This test also demonstrates that even at this high concentration of quaternary ammonium salt (Q1) alone, the number of organisms surviving initially decreases but after 24 and 72 hours the surviv-

EXAMPLE VIII

This test demonstrates the unexpected ability of the combination of a quaternary amine (Q1) with a 4-isothiazolin-3-one at concentrations of 50:25 to as low as 50:0.8 gives not only initial speed-of-kill but prolonged control as well. The result of this test are given in Table VIII below. This test further highlights the need for a complete control since any organisms surviving the useful life of the microbicides flourish on the nutrients present in the poultry manure. See the data in the eighth column (0.4 ppm I2) of Table VIII presented below.

E. coli and that this organism in fact flourishes in the presence of the poultry manure.

TABLE IX

| Quaternary Under Test | CONC. OF Q1 | CONC. OF I2 | CONC. MANURE* | No. of Organisms Surviving/ml. of Test Solution After: | | | | |
|---|---|---|---|---|---|---|---|---|
| | | | | 5 Min. | 10 Min. | 15 Min. | 30 Min. | 24 Hrs. |
| Q1 | 50 ppm | 50 ppm | 0.25% | | | 11,050 | 256 | 0 |
| Q2 | 50 ppm | 50 ppm | 0.25% | | | 4,940 | 72 | 0 |
| Q3 | 50 ppm | 50 ppm | 0.25% | | | 37,700 | 910 | 0 |
| Q4 | 50 ppm | 50 ppm | 0.25% | | | >100,000 | 52,650 | 0 |
| Q5 | 50 ppm | 50 ppm | 0.25% | | | >100,000 | 9,750 | 0 |
| Q1 | 50 ppm | None | 0.25% | | | >100,000 | >100,000 | >100,000 |
| Q2 | 50 ppm | None | 0.25% | | | 46,800 | 19,500 | >100,000 |
| Q3 | 50 ppm | None | 0.25% | | | >100,000 | >100,000 | >100,000 |
| Q4 | 50 ppm | None | 0.25% | | | 100,000 | >100,000 | >100,000 |
| Q5 | 50 ppm | None | 0.25% | | | >100,000 | >100,000 | >100,000 |
| Q6 | 400 ppm | None | 1.0% | 7,150 | 4,550 | Not read | 1,200 | >100,000 |
| Q6 | 400 ppm | 75 ppm | 1.0% | 2,050 | 208 | Not read | 1 | 0 |
| None | None | 75 ppm | 1.0% | >100,000 | >100,000 | Not read | >100,000 | 0 |
| None | None | 50 ppm | 0.25% | Not read | Not read | >100,000 | >100,000 | 0 |
| Control | None | None | 0.25% | | | >100,000 | >100,000 | >100,000 |

*Sterile dried ground poultry manure
No. of Organisms/ml. of Test Soln. at zero time = 10,500,000; Test Organism = E. Coli #11229

TABLE VIII

| CONC. OF Q1 | CONC. OF I2 | CONC. MANURE* | No. of Organisms Surviving/ml. of Test Solution After: | | | | | |
|---|---|---|---|---|---|---|---|---|
| | | | 5 Min. | 10 Min. | 30 Min. | 24 Hrs. | 48 Hrs. | 1 Wk. |
| 50 ppm | None | 0.25% | >100,000 | >100,000 | >100,000 | >100,000 | >100,000 | >100,000 |
| 50 ppm | 25 ppm | 0.25% | >100,000 | >100,000 | 2,210 | 0 | 0 | 0 |
| 50 ppm | 12.5 ppm | 0.25% | >100,000 | >100,000 | >10,000 | 0 | 0 | 0 |
| 50 ppm | 6.25 ppm | 0.25% | >100,000 | >100,000 | >100,000 | 0 | 0 | 0 |
| 50 ppm | 3.13 ppm | 0.25% | >100,000 | >100,000 | >100,000 | 0 | 0 | 0 |
| 50 ppm | 1.5 ppm | 0.25% | >100,000 | >100,000 | >100,000 | 1 | 0 | 0 |
| 50 ppm | 0.8 ppm | 0.25% | >100,000 | >100,000 | >100,000 | 32 | 1 | 0 |
| 50 ppm | 0.4 ppm | 0.25% | >100,000 | >100,000 | >100,000 | >10,000 | >100,000 | >100,000 |
| 50 ppm | 0.2 ppm | 0.25% | >100,000 | >100,000 | >100,000 | >100,000 | >100,000 | >100,000 |
| 50 ppm | 0.1 ppm | 0.25% | >100,000 | >100,000 | >100,000 | >100,000 | >100,000 | >100,000 |
| None | 25 ppm | 0.25% | >100,000 | >100,000 | >100,000 | 0 | 0 | 0 |
| None | 12.5 ppm | 0.25% | >100,000 | >100,000 | >100,000 | 0 | 0 | 0 |
| None | 6.25 ppm | 0.25% | >100,000 | >100,000 | >100,000 | 0 | 0 | 0 |
| None | 3.13 ppm | 0.25% | >100,000 | >100,000 | >100,000 | 0 | 0 | 0 |
| None | None | 0.25% | >100,000 | >100,000 | >100,000 | >100,000 | >100,000 | >100,000 |

*Sterile dried ground poultry manure
Test Organism = E. coli No. 11229
No. of Organisms/ml. of Test Soln. at zero time = 10,2500,000

EXAMPLE IX

This test demonstrates that the combination of various quaternary ammonium salts (Q1, Q2, Q3, Q4, Q5 and Q6) with the 4-isothiazolin-3-one (I2) exhibits unexpected speed-of-kill and prolonged control as compared to the same concentration of quaternary ammonium salt alone or the 4-isothiazolin-3-one alone. The results of this test are given below in Table IX. It can be seen that the quaternary ammonium salts alone do not control the

EXAMPLE X

This test shows the effect of poultry manure concentration on the quaternary ammonium salts and the effect of varying concentrations of quaternary ammonium salt (Q1) with two different 4-isothiazolin-3-ones (I1) and (I2). The results of these tests are given below in Table X. This table shows that the microbicidal activity of (Q1) is greatly impaired by the presence of poultry manure and again demonstrates the ability of the surviving organisms to multiply in the presence of the manure at concentrations much greater than those needed to give complete control in the absence of manure.

TABLE X

| Quaternary | Conc. Manure* | No. of Organisms/ml. of Test Solution After: | | |
|---|---|---|---|---|
| | | 10 min. | 30 min. | 24 hrs. |
| Q1 (50 ppm) | None | 0 | 0 | 0 |
| Q1 (50 ppm) | 0.25% | >100,000 | >100,000 | >100,000 |
| Q1 (50 ppm) | 1% | >100,000 | >100,000 | >100,000 |
| Q1 (100 ppm) | 1% | >100,000 | >100,000 | >100,000 |
| Q1 (200 ppm) | 1% | >104,900 | 81,900 | >100,000 |
| Q1 (400 ppm) | 1% | 182 | 189 | >100,000 |
| I1 (50 ppm) | 1% | >100,000 | >100,000 | 3,380 |
| Q1 (50 ppm) + I1(50 ppm) | 1% | >100,000 | >100,000 | 15,600 |
| Q1 (400 ppm) + I1(50 ppm) | 1% | >100,000 | >100,000 | 3,640 |
| Q1 (200 ppm) + I1(50 ppm) | 1% | 43,500 | 20,150 | 0 |
| Q1 (400 ppm) + I1(50 ppm) | 1% | 403 | 106 | 0 |

TABLE X-continued

| Quaternary | Conc. Manure* | No. of Organisms/ml. of Test Solution After: | | |
|---|---|---|---|---|
| | | 10 min. | 30 min. | 24 hrs. |
| I2 (50 ppm) | 1% | 19,500 | 910 | 0 |
| Q1 (500 ppm) + I2(50 ppm) | 1% | 12,700 | 314 | 0 |
| Q1 (100 ppm) + I2(50 ppm) | 1% | 3,510 | 75 | 0 |
| Q1 (200 ppm) + I2(50 ppm) | 1% | 281 | 0 | 0 |
| Q1 (400 ppm) + I2(50 ppm) | 1% | 5 | 0 | 0 |

*Sterile dried ground poultry manure
Test Organism = E. coli #11229

EXAMPLE XI

This test demonstrates that the combination of the quaternary ammonium salt (Q1) with various 4-isothiazolin-3-ones (I3, I5, I6 and I10) produce an unexpected speed-of-kill against E. coil in the presence of poultry manure as compared to the quaternary ammonium salt alone or the 4-isothiazolin-3-ones alone. The results of this test are given in Table XI below.

TABLE XI

| Isothiazolone Tested | Conc. Q1 | Conc. Isothiazolone | Conc. Manure | No. of Organisms Surviving/ml. of Test Soln. After: | | |
|---|---|---|---|---|---|---|
| | | | | 10 Min. | 30 Min. | 24 Hrs. |
| I3 | None | 50 ppm | 1.0% | >100,000 | 58,500 | 0 |
| | 400 ppm | 50 ppm | 1.0% | 46 | 0 | 0 |
| I4 | None | 50 ppm | 1.0% | 40,950 | 2,310 | 0 |
| | 400 ppm | 50 ppm | 1.0% | 0 | 0 | 0 |
| I5 | None | 50 ppm | 1.0% | >100,000 | 7,150 | 0 |
| | 400 ppm | 50 ppm | 1.0% | 83 | 0 | 0 |
| I6 | None | 50 ppm | 1.0% | 10,400 | 89 | 0 |
| | 400 ppm | 50 ppm | 1.0% | 0 | 0 | 0 |
| I10 | None | 50 ppm | 1.0% | >100,000 | >100,000 | 0 |
| | 400 ppm | 50 ppm | 1.0% | 20,450 | 329 | 0 |
| Q1 | 400 ppm | None | 1.0% | 500 | 280 | >100,000 |
| Control | None | None | 1.0% | >100,000 | >100,000 | >100,000 |

*Sterile dried ground poultry manure
Test Organism = E. coli
No. of Organisms/ml. of Test Soln. at zero time = 11,500,000

EXAMPLE XII

This test demonstrates that the combination of the quaternary ammonium salt (Q1) with various 4-isothiazolin-3-ones (I2, I13, I14, I21, I24 and I27) produce an unexpected speed-of-kill against S. aureus in the presence of poultry manure as compared to the quaternary ammonium salt alone or the 4-isothiazolin-3-ones alone. The results of this test are given below in Table XII.

EXAMPLE XIII

This test demonstrates that the combination of various quaternary ammonium salts (Q1, Q2, Q3, Q4, Q5 and Q6) with the 4-isothiazolin-3-one (I2) provides unexpected speed-of-kill as compared to the quaternary ammonium salts alone or the isothiazolone alone in the presence of poultry manure. This test again demonstrates that the quaternary ammonium salts alone in the presence of manure cannot control the test organism at the levels tested. The results of this test are given in Table XIII below. In this test plates containing 1,000,000 surviving organisms or less were counted and those containing greater than 1,000,000 surviving organisms were listed as 1,000,000 in order to present a better evaluation of the observed microbicidal effect. Moreover, this test differs from Example IX in that the tests were conducted at 1, 2, 3 and 4 hours in order to evaluate the microbicidal effect during the interval

TABLE XII

| Isothiazolone Test | Conc. Q1 | Conc. Isothiazolone | Conc. Manure* | No. of Organisms Surviving/ml. of Test Soln. After: | | | |
|---|---|---|---|---|---|---|---|
| | | | | 5 Min. | 10 Min. | 30 Min. | 24 Hrs. |
| I 13 | None | 50 ppm | 0.25% | 70,200 | 15,600 | 5,590 | 1 |
| | 50 ppm | 50 ppm | 0.25% | 0 | 0 | 0 | 0 |
| I 14 | None | 50 ppm | 0.25% | >100,000 | >100,000 | >100,000 | 1 |
| | 50 ppm | 50 ppm | 0.25% | 3 | 0 | 0 | 0 |
| I 21 | None | 50 ppm | 0.25% | >100,000 | >100,000 | >100,000 | >100,000 |
| | 50 ppm | 50 ppm | 0.25% | 30 | 8 | 2 | 0 |
| I 24 | None | 50 ppm | 0.25% | >100,000 | >100,000 | >100,000 | >100,000 |
| | 50 ppm | 50 ppm | 0.25% | 35 | 15 | 3 | 0 |
| I 27 | None | 50 ppm | 0.25% | 76,000 | 31,200 | 9,750 | 0 |
| | 50 ppm | 50 ppm | 0.25% | 7 | 2 | 0 | 0 |
| I 2 | None | 50 ppm | 0.25% | >100,000 | 81,900 | 26,650 | 10 |
| | 50 ppm | 50 ppm | 0.25% | 14 | 1 | 0 | 0 |
| Q1 | 50 ppm | None | 0.25% | 42 | 25 | 11 | 0 |
| Control | None | None | 0.25% | >100,000 | >100,000 | >100,000 | >100,000 |

*Sterile dried ground poultry manure
Test Organism = Staphylococcus aureus
No. of Staphylococcus aureus Organisms/ml. of Test Soln. at zero time = 6,200,000 between the 30 minutes and 24 hour tests shown in Example IX.

organism; and total counts of the organisms surviving after 24 hours exposure rather than the presence or

TABLE XIII

| Quat. Tested | Conc. Quat. | Conc. I2 | Conc. Manure* | No. of Organisms/ml. of Test Solution Surviving After Exposure Time of: | | | | |
|---|---|---|---|---|---|---|---|---|
| | | | | 1 Hour | 2 Hours | 3 Hours | 4 Hours | 24 Hours |
| Q1 | 50 ppm | None | 0.25% | 572,000 | 416,000 | 591,500 | 513,000 | >1,000,000 |
| Q2 | 50 ppm | None | 0.25% | 157,300 | 143,000 | 79,300 | 42,900 | >1,000,000 |
| Q3 | 50 ppm | None | 0.25% | 565,500 | 481,000 | 526,500 | 448,500 | >1,000,000 |
| Q4 | 50 ppm | None | 0.25% | >1,000,000 | >1,000,000 | >1,000,000 | >1,000,000 | >1,000,000 |
| Q5 | 50 ppm | None | 0.25% | >1,000,000 | >1,000,000 | >1,000,000 | >1,000,000 | >1,000,000 |
| Q6 | 50 ppm | None | 0.25% | 234,000 | 286,000 | 41,600 | 43,500 | >1,000,000 |
| None | — | 50 ppm | 0.25% | 102,700 | 33,200 | 13,500 | 5,300 | 0 |
| Q1 | 50 ppm | 50 ppm | 0.25% | 650 | 18 | 0 | 0 | 0 |
| Q2 | 50 ppm | 50 ppm | 0.25% | 730 | 10 | 0 | 0 | 0 |
| Q3 | 50 ppm | 50 ppm | 0.25% | 1,370 | 16 | 0 | 0 | 0 |
| Q4 | 50 ppm | 50 ppm | 0.25% | 14,400 | 1,690 | 72 | 41 | 0 |
| Q5 | 50 ppm | 50 ppm | 0.25% | 9,400 | 910 | 32 | 11 | 0 |
| Q6 | 50 ppm | 50 ppm | 0.25% | 118 | 17 | 0 | 0 | 0 |
| None | None | None | 0.25% | >1,000,000 | >1,000,000 | >1,000,000 | >1,000,000 | >1,000,000 |

*Sterile dried ground poultry manure
No. of E. coli #11229 Organisms/ml. of Test Soln. at zero time = 11,500,000

EXAMPLE XIV

This test demonstrates the microbicidal activity of the 4-isothiazolin-3-ones (I8, I15, I20, I22, I23 and I25) with the quaternary ammonium salt (Q1), 24 and 96 hours after treatment. This test demonstrates that these combinations also provide an unexpected speed-of-kill as compared to the corresponding quaternary ammonium salt alone or the 4-isothiazolin-3-ones alone. The results of this test are presented in Table XIV below. Again in this test the plates were counted at 1,000,000 surviving organisms or lower as in Example XIII.

absence of turbidity after 24 hours exposure are used to determine efficacy. We also employed sterile ground poultry manure in our studies to simulate the organic load which is almost always present to some degree in most of the intended applications for the combinations under study.

Under the conditions of the test employed, the particular combination of biocides examined by this procedure (Q1 and I8) failed to provide complete kill of the test inoculum in 24 hours. Therefore those concentrations of the biocides under test which provided 99.99% kill of the test inoculum were incorporated into the Kull

TABLE XIV

| Q1 | Isothiazolone | Conc. Q1 | Conc. Isothiazolone | Conc. Manure* | No. of Organisms/ml. of Test Solution Surviving After Exposure Time of: | |
|---|---|---|---|---|---|---|
| | | | | | 24 Hours | 96 Hours |
| None | I8 | None | 50 ppm | 0.15% | 22,500 | 0 |
| None | I15 | None | 50 ppm | 0.15% | >1,000,000 | >1,000,000 |
| None | I20 | None | 50 ppm | 0.15% | >1,000,000 | >1,000,000 |
| None | I22 | None | 50 ppm | 0.15% | >1,000,000 | >1,000,000 |
| None | I23 | None | 50 ppm | 0.15% | >1,000,000 | >1,000,000 |
| None | I25 | None | 50 ppm | 0.15% | >1,000,000 | >1,000,000 |
| Q1 | I8 | 50 ppm | 50 ppm | 0.15% | 0 | 0 |
| Q1 | I15 | 50 ppm | 50 ppm | 0.15% | 33,100 | 30,000 |
| Q1 | I20 | 50 ppm | 50 ppm | 0.15% | 71,500 | 58,500 |
| Q1 | I22 | 50 ppm | 50 ppm | 0.15% | 88,400 | 56,000 |
| Q1 | I23 | 50 ppm | 50 ppm | 0.15% | 59,800 | 4,800 |
| Q1 | I25 | 50 ppm | 50 ppm | 0.15% | 50,500 | 4,600 |
| Q1 | None | 50 ppm | None | 0.15% | >1,000,000 | >1,000,000 |
| None | None | None | None | 0.15% | >1,000,000 | >1,000,000 |

*Sterile dried ground poultry manure
No. of E. coli #11229 organisms/ml. of Test Soln. at zero time = 11,750,000

EXAMPLE XV

This test is a modification of the test described in U.S. Pat. No. 3,947,581 granted Mar. 30, 1976 to Paul Swerd et al. in columns 3 and 4 of that patent and that described in the publication APPLIED MICROBIOLOGY, vol. 9, page 539, (1961) by F. C. Kull et al. This test employed the Butterfield-Wattie Time Survival technique and applied the Kull formula for synergism to the data obtained. The Butterfield-Wattie Time Survival procedure is somewhat similar to the test procedure used by Kull, et al, with the exceptions that aqueous solutions of the biocides rather than nutrient broth solutions of the biocides are inoculated with the test formula for determination of synergism. A kill of 99.9% of an inoculum containing at least 1,000,000 organisms is currently recognized by the U.S. Government (EPA) as sufficient to register a germicide for use as a surface sanitizer.

The results of this test are given in Table XV below. As discussed in the above cited literature, if the sum of the ratios for a mixture $Q_A/Q_a + Q_B/Q_b = 1$, additivity is indicated; if it is $<1$, synergism has occurred; a value of $>1$ is indicative of antagonism. Using the data in Table XI below, the sum of the ratios of the mixtures is equal to 0.25 and 0.375, respectively, see calculations below. Therefore the observed effect of the combinations of quaternary ammonium salts and 4-isothiazolin-3-ones is synergistic.

TABLE XV

| | Conc. Q1 (ppm) | Conc. I8 (ppm) | Ma- nure* | No. of Organisms Surviving/ml.of Test Solutions After 24 Hours | % Kill |
|---|---|---|---|---|---|
| Quaternary | 50 | — | 0.25% | >1,000,000 | <90,000 |
| Q1 | 100 | — | 0.25% | 1,160,000 | 88.63 |
| Q1 | 200 | — | 0.25% | 92,300 | 99.10 |
| Q1 | 400 | — | 0.25% | 0 | 100.00 |
| Isothia-zolone | — | 25 | 0.25% | 260,000 | 97.45 |
| I8 | — | 50 | 0.25% | 46,000 | 99.55 |
| I8 | — | 100 | 0.25% | 2,370 | 99.98 |
| I8 | — | 200 | 0.25% | 420 | >99.99 |
| I8 | — | 400 | 0.25% | 55 | >99.99 |
| Q1 + I8 | 50 | 25 | 0.25% | 254 | >99.99 |
| Q1 + I8 | 50 | 50 | 0.25% | 15 | >99.99 |
| Control | — | — | 0.25% | >1,000,000 | <90.00 |

*Sterile dried ground poultry manure
No. of E. coli #11229 organisms/ml. of Test Soln. at zero time = 10,200,000

$$\frac{QA}{Qa} + \frac{QB}{Qb}$$

QA = Quantity of cmpd. A in the mixture producing an endpoint
Qa = Quantity of cmpd. A acting alone to produce an endpoint
QB = Quantity of cmpd. B in the mixture producing an endpoint
Qb = Quantity of cmpd. B acting alone to produce an endpoint
Compound A = Isothiazolone I8
Compound B = Quaternary Q1
Thus taking data from Table XI for Q1 (50 ppm) + I8 (25 ppm)

$$\frac{QA\ (25)}{Qa\ (200)} + \frac{QB\ (50)}{Qb\ (400)} = 0.125 + 0.125 = 0.25$$

$$\frac{QA\ (50)}{Qa\ (200)} + \frac{QB\ (50)}{Qb\ (400)} = 0.25 + 0.125 = 0.375$$

When evaluated by the procedure of Example I, compositions combining other isothiazolinones of Formulas I and II with typical bactericidal quaternary ammonium salts possess synergistic bactericidal activity.

It is to be understood that changes and variations may be made without departing from the spirit and scope of the invention as defined by the appended claims.

I claim:

1. A synergistic bactericidal composition comprising an isothiazolinone or its acid addition salt having the formula

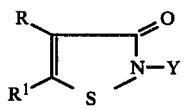

wherein
Y is $(C_1-C_8)$alkyl, cyclohexyl, phenyl or benzyl or phenyl or benzyl substituted with up to two halogen atoms;
R is a methyl group, a hydrogen atom or a halogen atom; and
R' is a hydrogen atom or a halogen atom;
and a bactericidal quaternary ammonium salt wherein the quaternary ammonium salt is selected from the group consisting of:
(a) n-alkyl ($C_{14}$:50%; $C_{12}$:40%; $C_{16}$:10%)dimethylbenzylammonium chloride;
(b) a mixture of 50% by weight alkyl ($C_{14}$:60%; $C_{16}$:30%; $C_{12}$:5%; $C_{18}$:5%)dimethylbenzylammonium chloride; and 50% alkyl ($C_{12}$:50%; $C_{14}$:30%; $C_{16}$:17%; $C_{18}$:3%)dimethylethylbenzylammonium chloride;
(c) a mixture of (n-$C_8$ to n-$C_{18}$)alkyldimethylbenzylammonium chlorides containing not less than 40% by weight n-$C_{12}$ alkyl, not less than 20% n-$C_{14}$ alkyl and not less than 70% by weight total of n-$C_{12}$ and n-$C_{14}$ alkyl;
(d) p-diisobutylphenoxyethoxyethyldimethylbenzylammonium chloride;
(e) a mixture of 80% by weight of methyldodecylbenzyltrimethylammonium chloride and 20% of methyldodecylxylylenebis(trimethyl)ammonium chloride;
(f) di-n-alkyl ($C_8$–$C_{11}$ n-alkyl, average $C_{10}$) dimethylammonium chloride; and
the weight ratio of the 4-isothiazolin-3-one to the quaternary ammonium salt is from 5:1 to 1:50.

2. The composition of claim 1 wherein the 4-isothiazolin-3-one is a metal salt complex of the formula

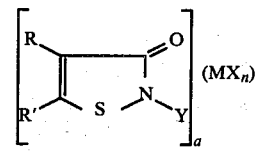

wherein
M is a cation of a metal, such as barium, cadmium, calcium, chromium, cobalt, copper, iron, lead, lithium, magnesium, manganese, mercury, nickel, sodium, silver, strontium, tin, zinc, or the like;
X is an anion forming a compound with the cation M, wherein the compound has sufficient solubility to form a metal salt complex;
a is the integer 1 or 2; and
n is an integer which for the anion X satisfies the valence of the cation M.

3. The composition of claim 1 wherein the quaternary ammonium salt is a mixture of n-$C_{12}$ alkyldimethylbenzylammonium chloride, n-$C_{14}$ alkyldimethylbenzylammonium chloride, and n-$C_{16}$ alkyldimethylbenzylammonium chloride.

4. The composition of claim 3 wherein the 4-isothiazolin-3-one is the calcium chloride complex of 5-chloro-2-methyl-4-isothiazolin-3-one.

5. The composition of claim 3 wherein the 4-isothiazolin-3-one is 4,5-dichloro-2-cyclohexyl-4-isothiazolin-3-one.

6. The composition of claim 3 wherein the 4-isothiazolin-3-one is 5-chloro-4-methyl-2-(3-chloro phenyl)-4-isothiazolin-3-one.

7. A method of controlling bacteria in the presence of organic matter which comprises applying thereto an effective amount of the composition of claim 1.

8. A method of protecting a locus from bactericidal contamination in the presence of organic matter which comprises applying to the locus an effective amount of the composition of claim 1.

* * * * *